(12) United States Patent
Exner et al.

(10) Patent No.: US 6,288,026 B1
(45) Date of Patent: Sep. 11, 2001

(54) PROCESS AND COMPOSITION FOR TREATING DISEASES WITH AN OIL-IN-WATER EMULSION

(76) Inventors: Heinrich Exner, Birkenweg 29, 39291 Möckern; Peter Klose, Pietzpuhler Weg 4,m, 39291 Grabow, both of (DE)

( * ) Notice: Subject to any disclaimer, the term of this patent is extended or adjusted under 35 U.S.C. 154(b) by 0 days.

(21) Appl. No.: 09/511,807

(22) Filed: Feb. 23, 2000

Related U.S. Application Data
(60) Provisional application No. 60/121,583, filed on Feb. 24, 1999.

(51) Int. Cl.[7] .................................................. A61K 38/00
(52) U.S. Cl. .................. 514/2; 514/12; 514/21; 424/184.1; 424/185.1
(58) Field of Search .............. 424/282.1, 278.1, 424/243.1, 201.1, 184.1, 185.1, 197.11, 78.17; 514/12.2, 21

(56) References Cited

U.S. PATENT DOCUMENTS 5,904,925 * 5/1999 Exner .................................. 424/282.1

* cited by examiner

*Primary Examiner*—Avis M. Davenport
(74) *Attorney, Agent, or Firm*—Gabriel P. Katona L.L.P.

(57) ABSTRACT

The invention concerns a process for treating systemic inflammatory response syndrome (SIRS), intensive care requiring conditions, viral diseases, Colitis ulcerosa, Crohn's disease, Parkinson's disease, Alzheimer's disease, multiple sclerosis, infectious hospital polyresistance conditions of viral and bacterial sources (infections hospitalismus), bronchial asthma, kidney and urethral infections, migraines, rheumatoid arthritis, osteoporosis Sudeck, acute and chronic inflammations, venal and arterial inflammations, acute and chronic exhaustion conditions, tumors, muscle shrinkage diseases, hemorrhoids, chemically induced heart diseases, hypertonia, aging phenomena, acute and chronic pain conditions, spastics, polyneuropathies, prostate neoplasms, hair loss, impotence, neurodermitis, cervical syndrome, tissue traumas, and amyotropic lateral sclerosis (Lou Gehrig's disease), which comprises administering to a patient in need therefor an effective amount of Paravac composition which can suitably comprise in g/ml of 0.01–0.03 polydimethylsiloxane with a polymerization degree of 20–400 and a kinematic viscosity of 20–1300 $mm^{2/s}$, 0.0–1–0.03 dimethylsulfoxide, 0.03–0.06 of a hydrophilic emulsifier, and 0.86–0.95 isotonic salt solution, and optionally 0.0001–0.01 Na or Ca salt of EDTA as a chelating agent.

10 Claims, No Drawings

PROCESS AND COMPOSITION FOR TREATING DISEASES WITH AN OIL-IN-WATER EMULSION

This is a nonprovisional application based on provisional patent application No. 60/121,583, filed on Feb. 24, 1999.

FIELD OF INVENTION

The present invention relates to a process and composition for the treatment of various diseases with an oil-in-water emulsion.

BACKGROUND

U.S. Pat. No. 5,904,925 describes an oil-in-water emulsion as an incomplete and a complete adjuvant for antigens, which comprises from 0.01% to 30% of a polydimethylsiloxane, from 0.01 to 15% of a complex emulsifier with an HLB of 9016, from 45% to 99% of a pharmaceutically acceptable salt solution, from 0.01% to 10 of dimethylsulfoxide, and from 0.0001% to 1% of a chelating agent (the foregoing incomplete adjuvant of U.S. Pat. No. 5,904,925 being hereinafter referred to as "Paravac"). Peptidoglycans of species-specific *Staphylococcus aureus* strains and/or of other strains can be added to this incomplete adjuvant composition for immunization, in a concentration of from 0.00001 to 1 mg protein per ml adjuvant, and water soluble natural and/or synthetic polymers in a concentration of from 0.0001 to 10 mg/ml of the adjuvant. The patent also discloses the use of that adjuvant against a variety of diseases, and this application is a further development and a completion of that earlier invention. Thus any reference herein to a "Paravac" emulsion or composition, other than in the specific examples, is intended to encompass both the incomplete and the complete adjuvant compositions of U.S. Pat. No. 5,904,925.

That earlier invention provided adjuvancies which by combination with immunizing antigens or in combination with peptidoglycans into a pharmaceutically acceptable formulation will stimulate the defense mechanisms of the body to such an extent that in addition to the active immune prophylaxis also weak antigens produce a general and specific immunotherapy. Good results are obtained with this adjuvant in immunotherapy. It is a drawback that the preparation of the complete adjuvant, or the adding of proteins have relatively substantial requirements. The danger of an anaphylactic reaction in the host is a pathophysiological drawback of the complete adjuvant in the case of repeated use.

DESCRIPTION OF THE INVENTION

It is an object of the invention to provide a process for treating or for preventing the occurrence of certain diseases with an oil-in-water emulsion as an adjuvant for parenteral, especially intramuscular application, which is free from proteins as an incomplete adjuvant, by itself, or in combination with other parenterally applicable agents or in combination with a protein, in the for of a completre adjuvant. The diseases treated by the process of the present invention are systemic inflammatory response syndrome (SIRS), intensive care requiring conditions, viral diseases including hepatitis C and AIDS, Colitis ulcerosa, Crohn's disease, Parkinson's disease, Alzheimer's disease, multiple sclerosis, infectious hospital polyresistance conditions of viral and bacterial sources (infections hospitalismus), bronchial asthma, kidney and urethral infections, migraines, rheumatoid arthritis, osteoporosis Sudeck, acute and chronic inflammations, venal and arterial inflammations, acute and chronic exhaustion conditions, tumors, muscle shrinkage diseases, hemorrhoids, chemically induced heart diseases, hypertonia, aging phenomena, acute and chronic pain conditions, spastics, polyneuropathies, prostate neoplasms, hair loss, impotence, neurodermitis, cervical syndrome, tissue traumas, and amyotropic lateral sclerosis (Lou Gehrig's disease).

As used throughout the specification and the claims (other than in the specific treatment examples), any reference to the "treating" of any disease, is also meant to include prophylactic application against the disease.

It was found that the aforementioned oil-in-water Paravac emulsion produces upon parenteral, especially intramuscular or subcutaneous application surprisingly good effects for the enumerated and other indications, with durable improvements. It was also found that the duration of the treatment until initial effects can be observed, is substantially shorter than in the case of conventional, targeted medications for each of the specific indications. Furthermore, the total period of treatment, as well as until initial improvements are observed, can all be substantially reduced, and no side effects were observed.

Application of the present invention leads to desired results also in the case of indications which have been heretofore considered to be "uncurable.", specifically in the case of hepatitis C, Parkinson's disease, Alzheimer's disease, multiple sclerosis, tumors, prostate neoplastics, and the like. In the case of patients for whom conventional drug therapy did not produce healing or relief and were considered refractory to conventional drug therapy, application of the present invention has frequently produced unexpected improved results.

The incomplete adjuvant Paravac is suitably formed into a silicone oil emulsion of an oil-in-water emulsion type, such as in g/ml of from about 0.01 to about 0.03 polydimethylsiloxane with a polymerization degree of from about 20 to about 400 and a kinematic viscosity of from about 20 to about 1300 $mm^{2/s}$; from about 0.01 to about 0.03 dimethylsulfoxide; from about 0.03 to about 0.06 of a hydrophilic emulsifier such as from about 25 to about 35% sorbitantrioleate, from about 25 to about 35% cetylstearylalcohol, and from about 35 to about 45% polysorbate 80; and from about 0.86 to about 0.95 isotonic salt solution, and optionally from about 0.0001 to about 0.01 Na or Ca salt of EDTA as a chelating agent. The following embodiment of the Paravac emulsion was used in the following examples; wherein the components are given in mass proportions (g/ml emulsion):

0.015 dimethicone 200,
0.015 dimethylsulfoxide,
0.015 sorbitantrioleate,
0.015 cetylstearylalcohol,
0.02 Polysorbate 80,
0.0002 Na/CA salt of ethylenediaminetetraacetic acid, and
0.9 isotonic NaCl solution (0.9% NaCl in water).

In addition to the foregoing components, the emulsion can also contain 0.02 g/ml glycerol.

It was found that the oil-in-water Paravac emulsion when applied alone intramuscularly or subcutaneously, has produced surprisingly good results with the aforementioned diseases, and also produced a durable effect. When Paravac was applied in combination with other pharmacologically active ingredients, further surprising benefits were obtained.

Thus the addition to Paravac of antibiotics, corticoids, antiparkinsonian agents, multiple sclerosis treating agents, neuro- and psychopharmaceutical agents, immunostimulants, and analgesics, can bring about a reduction of the conventional drug dose by up to 60%, and this permits a reduction of certain undesirable side effects of these agents.

The following examples further support and illustrate the process of the present invention. The Paravac composition that was used in the following examples was in mg/ml 0.015 dimethicone 200, 0.015 dimethylsulfoxide, 0.015 sorbitantrioleate, 0.015 cetylstearylalcohol, 0.02 Polysorbate 80, 0.0002 Na/CA salt of ethylenediaminetetraacetic acid, and 0.9 isotonic NaCl solution (0.9% NaCl in water).

The paravac composition was administered, depending on the nature of the treated disease, in 3–7, possibly 14 day intervals until stabilization of the health of the patient, and leukocytes, as well as CD4, CD8, NK, and TNF-α values were stabilized at normal levels. These levels were generally achieved depending on the severity of the disease and the age of the patient, after two to four weeks of treatment.

After the application of the treatment for from about 3 to about 7 days, treatment was generally continued within a from about 7 to about 14 days time period of each other. After clinical stabilization was achieved, i.e. a stable clinically improved condition, the time period between applications was extended for a from about 4 to about 6 weeks period to about every 14 days. Multiple injections can be made few hours apart from each other in the initialization of treatment.

Restitution of damaged tissues required a treatment of at least 6 to 12 months, and in the case of bone damage or disease, an even longer period of treatment was required.

In the case of chronic conditions, such as Parkinson's disease, multiple sclerosis, rheumatoid arthritis, therapy needed to be continued by the application of a steady maintenance dose every two to three weeks to prevent exacerbation of the disease.

EXAMPLE 1

Chronic Polyarthritis

The 60 year old female patient suffered for many years from chronic, and painful polyarthritis, as well as from osteoporosis and back pain.

At the initial consultation a pervasive illness was diagnosed of a rheumatoid nature, the patient was oedemous, joints were swollen, strong pains manifested themselves, and the patient could hardly move her extremities. The patient was not in condition to perform even simple activities. This condition has worsened in its development over a 5 month period. Common medication did not provide relief and have caused substantial undesirable side effects which she could no longer tolerate.

Injections of the Paravac emulsion were commenced with a 3 times daily for 5 days of 1 ml each, and continued thereafter weekly. The intensive pain of the patient was also medicated by Prednisolone (5 mg/2.5 mg/2.5 mg daily) and sleep was drug assisted at night.

For the first week the pains became tolerable, and after 6 weeks only pain in the leg occurred. The patient could again lift her arms above her head, and no side effects were observed.

EXAMPLE 2

Neurodermitis

A 36 year old female patient suffered from neurodermitis on her face, her breasts, the arms as well as experienced hair loss. The sharply distinctive neuridermitis condition persisted for 2 years. The condition has steadily worsened during the last months., especially in the face and the eyelids were affected.

Treatment took place once a week with the Paravac emulsion, by injecting her intramuscularly with 1 ml. After 6 weeks the symptoms started to recede and the symptoms have no longer worsened. The efflorescences on the face and on the throat began to smoothen, and to shrink in size.

After 10 weeks the Paravac emulsion was administered only biweekly and the patient's condition improved, the skin lesions have hardly itched and were visible briefly only upon contact with chemicals. After a 4 month treatment the patient appeared healed and no neurodermitis was visible at all. The patient was not given or administered to her skin any other creams or drugs, and reported a general improvement in her condition and well being, and productive capacity. She required less sleep, and became physically and psychologically more refractory. She suffered no longer from periodic headaches, and generally felt better, particularly in the mornings. No more hair loss took place after 6 weeks of treatment.

Application of the Paravac emulsion was terminated, and no worsening of the patient's condition could be observed. Neurodermitis has not returned, and bodily performing ability continues unabated without any side effects.

EXAMPLE 3

Parkinson's Disease, Gonarthrosis, Adipositas

A female patient, 74 years of age, suffered from Parkinson's disease, pervasive gonarthrosis, and adipositas. The Parkinson's disease symptoms have lasted for many years which have largely substantially worsened. She was able to walk only for short distances, such as 10 meters, and then had to sit down and rest. She was unable to leave her house without assistance. Her hands steadily trembled and all movements were accompanied by sharp pain in her back and her knees. The patient was unable to perform even the simplest household tasks. The lower thighs were oedemous particularly on the left side. Occasional nycturia was experienced. The blood pressure was 140/70, and this condition developed within 6 months before her first visit.

Treatment with a Paravac emulsion was commenced in weekly intervals with an administration of 1 ml each time.

After 8 weeks the patient's condition has substantially improved, she was able to walk several times the distance that she was able to walk before, she was able to carry out household tasks, knee pain was hardly experienced at all, and the back pain was present to a much lesser extent, and in spite of a slight cold the patient's conditions have not worsened. After 4 months of treatment the patient could walk up to 400 meters several times each day, she was considerably more durable, required less sleep, and was able to visit medical treatment site on her own, without any assistance. The injections produced no side effects or any local reactions or any general reactions such as infection-like symptoms. A maintenance dose is continued to be administered biweekly.

EXAMPLE 4

Migraines

A 40 year old female patient, and married mother of 2 children suffered from migraines since her 13th year. Initially the attacks occurred only for short periods, which after taking 1–2 pills have terminated within a few hours. After the attacks began to come more regularly, most often during menses, and often also on weekends. During pregnancies the attacks became more pronounced, because no medication was administered. Between age 20 and 30 the patient visited about 10 different specialists in the field of migraine research, and has taken many kinds of drugs. The attacks by that time lasted for 3 to 4 days and occurred frequently twice each month, required her to take up to 20 tablets each month. She has also tried acupuncture, but without any success. The pains were often intolerable and presented a most substantial burden on the patient and her family.

Treatment with a Paravac emulsion commenced biweekly, each with the administration of 1 ml of the emulsion. Already upon the first injection the contemporaneous commencement of a migraine attack was broken off. Thereafter the next customary attacks lasted for a much shorter duration and manifested themselves as brief, light headaches which did not even approximate the earlier migraine sensations. Later no more migraine symptoms could be observed at all, and between the 8th and 10th days after commencement of treatment only very brief headaches were observed.

Menstruation is more intensive and of shorter duration since the beginning of treatment, and the associated sensations have become more tolerable. After a 6 month period of treatment the patient was able to spend her first vacation since the birth of her children. Her health conditions have stabilized, and illnesses, such as the grippe progress substantially smoothly, and more briefly, and an earlier tendency to gastritis in the case of stress, has also vanished. A maintenance dose continues to be administered every three weeks.

EXAMPLE 5

Multiple Sclerosis

A female patient of 50 years of age on disablement retirement suffers from multiple sclerosis. This condition existed for the last 10 years, but the first symptoms occurred already in her teens. Progression occurred with increasing paralysis of the left arm and legs. The symptoms included a progressive loss of sight in the right eye. All earlier efforts with cortisone and interferon, etc. had not halted the gradual deterioration. For the last year the patient was unable to fend for her own needs and to care for herself, and no other treatment efforts brought any relief. All therapy efforts were halted, and the patient was simply waiting for her life to end.

A Paravac emulsion was administered to the patient once each week, with 1 ml of the emulsion, and the patient was under the control of an ophthalmologist, her own physician, and a neurologist, with continued clinical and laboratory checks. After 14 days the patient subjectively noticeably strengthened, both in her affected leg and arm could sleep better and leg spasms were rarely noticed. After a 5 week treatment the blue discoloration in the left arm due to inactivity, has vanished, the patient stumbled considerably less frequently, and the weakness (peroneus) in the left leg has remarkably lessened. She was able to take on a greater load of tasks thereafter.

After 10 weeks of treatment the patient was able with the support of an accompanying person to walk a kilometer, whereas before treatment she could walk a maximum of 200 meters, and all swallowing difficulties have disappeared. After 14 weeks of treatment the patient's general condition and mobility have substantially further improved. She was able to lift her arms above her head, the strength of her hands was substantially increased, and the patient could perform all household tasks by herself. Her walk became steadier, she suffered no longer from headaches, and had no cramps. The clinical symptoms of multiple sclerosis have vanished, and after a year of treatment with the Paravac emulsion her physical and psychological condition was so well restored that she was considered to be practically a healthy person. Her comfortable walking distance increased to 2 kilometers, and the ophthalmologist diagnosed a complete restoration of the condition of her optic nerve.

Due to a major operation to remove excess material from under the left lower thigh, a 3-day injection regimen of the Paravac emulsion was undertaken. The operation took place unproblematically, without any side effect of multiple sclerosis character. A maintenance dose of biweekly injections with the emulsion is continued.

EXAMPLE 6

Chronic Asthma, Hay Fever, Allergies

A 33 year old female patient suffered from childhood from many allergies, and in the last 3 years developed a bad asthma. The patient administers daily medication of broncholityc and asthma spray, whereby the spray is administered every 2 hours. She is unable to sleep due to breathing difficulties and the need to inhaling treatments, and suffers from acute asthma attacks about monthly. The emergency physician has to be called regularly, about once each month, when spraying and medication did not provide any relief. The patient's ability to deal with her household is seriously impaired, she cannot climb any stairs, and is badly affected by changes in the weather.

Treatment with a Paravac emulsion was started at weekly intervals by the injection of 1 ml each. Already after the third injection the patient's performance level improved, and she required fewer broncholytic/antiasthmatic applications. After the 6th injection the initial daily 5–6 sprays were reduced to 1–2 per day. The patient could sleep for entire night, and her daily performance level has constantly improved. No further allergic reactions were observed and the intake various medications was reduced by about 50%. From the 6th week onward a maintenance dose is administered every 10 to 14 days.

EXAMPLE 7

Parkinson's Disease

A 50 year old male patient, retired on disability pension, suffered from Parkinson's disease since age 37 when his fine motor functions in his right hand have disappeared. Various attempted treatments have failed, and the disease has progressed since then to the point where paralysis and cramps have occurred more often and lasted as long as 20 hours. After each attack a clonus occurred for about ½ hour, along with disturbed sleep. The frequency of administering medications was increased to the maximum permitted doses. The patient was unable to perform even the lightest kind of work.

Treatment with the Paravac emulsion was administered weekly with an injection of 1 ml each. After 5 weeks signs of improvement could be observed. No more difficult crises (cramps followed by paralysis) occurred, and no additional drug treatment was required. There were no local or general side effects or tolerance difficulties associated with the Paravac injections.

EXAMPLE 8

Osteoporosis Sudeck

A female patient of 48 years of age suffered from childhood from a tendency of infections, frequently grippal infections and furunculosis. The right wrist painfully swelled within a few days to inhibited wrist motion. Treatment with analgesics, cold compresses, cortisone, hospital stay, Rivanol compresses relieved some acute symptoms, and hand mobility improved, but the general clinical conditions did not. Indurations of muscles and tendons of the hand led to a functio lāsa. After manifestations of advance osteoporosis Sudeck were determined, the patient was admitted to a specialized osteoporosis hospital. In addition to symptomatic treatment only physiotherapy was applied. the patient was then able to function in the home without assistance, but only for a brief period. After about 6 months the patient's general condition has substantially worsened; the weight of the patient sank to 38 kg and was no longer able to perform household tasks due to a stiffening of all large joints; hair and hair color loss on the head, and a thinning and paling of the outer skin layers.

About 2 years after the initial appearance of symptoms the patient was first treated in 2–3 week intervals with 1 ml injections of a paravac emulsion. After about 6–8 weeks the joint pain was substantially reduced and their mobility has returned. The patient steadily acquired an improved quality of life with a better mental condition, After a year of treatment strong hair grew back on the head, pigmented hair replaced unpigmented hair, skin has tightened and became elastic due to a filling out of the underlaying fatty tissues. The patient is healed in body and mind and feels well. No negative effects occurred.

EXAMPLE 9

Crohn's Disease

A 54 year old male of 176 cm height and 65 kg weight has pale skin, declining tonus, strong bone and muscle pain, no durability, corrected dental layout with loose teeth, grey hair, tired mind and partially depressed, enteritic symptoms with rectal weakness, disturbed sleep, and sensitivity to infections.

1 ml Paravac emulsion injections were administered every two weeks. After 4–6 weeks the enteric symptoms improved and the earlier weight loss stagnated and with identical nourishment intake began to turn around. Sleep disturbances ceased, and longer, refreshing periods of sleep occurred. After ¼ of a year the rheumatoid muscle and bone pains which were resent with varying intensity from age 10, have substantially receded. After about ½ year the patient's original weight of 85 kg was achieved. Shoulder circumference and upper arm diameter grew by substantial muscle mass. The teeth strengthened within their holding cage. The hairs on the head and on the eyebrows were replaced by hairs of the original thickness, and the gradual replacement of grey hairs and stronger hair and nail growths were observed.

After 1 year performance has far improved beyond the stage of performance levels a the start of the fifth decade of age. Mental capacity and learning ability compared favorably to younger test subjects, grey hairs became replaced by hair pigmented darker than the original hair color. Aging processes started to stagnate, and all organs recovered their original functionality. A marked improvement was observed in the utilization of food, necessitating a weight control regimen. The redox system or the organism have also been regenerated thus, for example, resistance to sunlight was markedly improved. The typical perspiration odor was no longer present, and the skin is elastic, stretched, and has a healthy color. Treatment is continued every two to three weeks.

EXAMPLE 10

Hemorrhoids

A 32 year old female patient suffers from hemorrhoids. She was injected intramuscularly weekly with 0.5 ml of the Paravac emulsion. After 6 weeks the initial improvement could be observed, and the therapy was terminated after 16 months without any residual symptoms.

EXAMPLE 11

Neumonia with Chronic Exhaustion Condition

A 44 year old male patient suffers from pneumonia in connection with chronic exhaustion. Treatment with the Paravac emulsion took place biweekly, with intramuscular administration of 1 ml each. After 6 weeks an improvement became evident, and after 1 year the frequency of injections was increased for a 12 month period to a weekly dose, and thereafter the therapy was terminated. The patient is free from all symptoms and complaints.

EXAMPLE 12

Postmenopausal Complaints, Hot Flashes, Migraines

A 52 year old female patient suffered for years from postmenopausal complaints, hot flashes, and migraines. Treatment with a Paravac emulsion injection took place weekly for 1 year; with the patient receiving 1 ml injection each time. The first effects could be observed after about 8 weeks of treatment, and after 1 year the frequency of administration was reduced to biweekly administration for 18 months. Therapy was terminated after a total of 30 months, at which time the patient was free of all symptoms.

EXAMPLE 13

Chronic Lumbago, Chronic Cervical Syndrome

A male patient, age 40, suffered for a long existing chronic lumbago, and a chronic cervical syndrome. Treatment with a Paravac emulsion followed for 1 year initially in weekly, and later in biweekly intervals, with 1 ml Paravac being injected each time. Initial treatment commenced with the Paravac emulsion being combined with a steroidal analgesic for the first 4 injections, and thereafter with a nonsteroidal (NSAID) analgesic. The first effects manifested themselves within 8 weeks, followed by a steady improvement. After a 30 months treatment the patient is free from all complaints.

EXAMPLE 14

Hair Loss, Skin Pigmentation Disturbances

A 43 year old female patient suffers from hair loss and skin pigmentation disturbances. Treatment with Paravac emulsion injections took place for 11 months biweekly with 0.5 ml injections each time. After about 8 weeks the first results could be observed, with a steady improvement since then. Therapy was successfully terminated after 11 months, with the patient being symptom free.

EXAMPLE 15

Impotence

A 66 year old male patient suffered from erectile dysfunction. Paravac treatment took place weekly for 18 months, with the patient receiving 1 ml each time during the first three months, and 0.5 ml thereafter. After 8 weeks an elevation of performance manifested itself, and the improved results could be maintained since then.

EXAMPLE 16

Hypotonia

A female patient of 27 years age suffered for years from hypotonia, especially during the menstrual cycle. Paravac treatment took place for 1 year weekly and thereafter for 19 months biweekly with 0.5 ml being injected each time. Initial improvement could be observed within 4 weeks, and since then blood pressure became normalized during the menstrual cycle.

EXAMPLE 17

Chronic-Ischemic Heart Disease

A 76 year old male patient suffered for many years from chronic ischaemia. Paravac treatment was started with weekly injections for 8 weeks, and thereafter biweekly for 6 months, with 0.5 ml administered each time. First improvements manifested themselves after 3 months, and the performing ability of the patient has steadily increased since then, and his other medications need no further increase.

EXAMPLE 18

Joint Pains

A 49 year old female patient suffered for a long time from joint pains. Paravac injections were commenced for 27 months every 10–14 days, with 0.5 ml being injected each time. First improvement could be observed after 8 weeks, then the pains have entirely vanished and no new pains occurred. During Paravac treatment the customary antirheumatic cortisone therapeutic medication dose of the patient was reduced by 50%.

EXAMPLE 19

Prostate Cancer, Bladder Infection

A 64 year old male patient suffered from prostate cancer and had an infected bladder. Treatment took place over 24 months with 0.5 ml Paravac emulsion being injected every two weeks. For the first 4 Paravac injections, the emulsion was combined with an antibiotic against the bacteria causing the bladder infection. After 6 weeks the infection has improved, and after 2 years of treatment the tumor was no longer detectable. The prior antibiotic dosage could be reduced during the Paravac administration regimen by ⅔, while maintaining higher efficacy. Biweekly treatment is continuing.

EXAMPLE 20

Lateral Sclerosis

A 55 year old male patient suffers from amyotropic lateral sclerosis (Lou Gehrig's disease). Treatment with the Paravac emulsion was started for 2 months by injecting 1 ml of the emulsion every 10–14 days, and then every 7 and then alternately 3 days thereafter. Treatment continued since the last 2 years, and the progression of the disease was markedly reduced, however, without any noticeable other improvement.

EXAMPLE 21

Hepatitis C

A female, 44 year old patient suffers from hepatitis C. The first 4 Paravac injections were administered spaced 3 days from each other, and thereafter weekly 1 ml each. The initial beneficial effects were observed after 4 weeks. After 6 months of treatment, the dose was reduced to a biweekly 0.5 ml. During the rest of the treatment of 18 months no recidivism was noticeable.

EXAMPLE 22

SIRS Following Soiled Peritonitis

The 21 year old male patient has soiled peritonitis due to perforation of the appendix and had breathing difficulties. Injections with a Paravac emulsion are started at 1 ml each every 3 days. A first effect could be noticed after 3 injections, and after 5 injections the patient no longer had any breathing difficulties, the oedema and all other symptoms were receding.

EXAMPLE 23

Bronchial Asthma

A 66 year old female patient suffered for years from bronchial asthma. Weekly Paravac injections commenced at the rate of 0.5 ml. Initial beneficial effects could be recognized after 6 weeks. After 1 year of treatment the patient manifested good physical and mental performing ability and with a steady breathing ability could discontinue all other medications. Over the total 16 month course of the Paravac treatment no infections occurred.

EXAMPLE 24

Colitis Ulcerosa, Migraines

A 47 year old female patient suffers from colitis ulcerosa and migraines. Paravac injections were commenced at the rate of 0.5 ml every 4 days for the first 4 weeks, and thereafter at weekly intervals for 5 months, and finally biweekly. Initial beneficial effects manifested themselves after 3 weeks. During the 16 month period of the therapy no recidivist tendencies were noticed.

EXAMPLE 25

Allergies, Chronic Skin Inflammations, and Headaches

A 86 year old female patient suffered from chronic skin inflammations, and headaches. Paravac injections were started at a weekly rate of 0.5 ml each. An initial beneficial effect could be observed after 3 weeks of treatment, and a steady improvement was observed after a course of a 4 month treatment.

EXAMPLE 26

Phlebitis and Varicosis on Both Legs

A 54 years old female patient suffered on both legs from phlebitis, and varicosis. Injections were administered at the rate of 0.5 ml weekly for the first 7 weeks, and then 0.5 ml each for 9 months every 10–14 days. Initial beneficial effects became noticeable after 4 weeks of treatment, and within 11 months after a brief recidivismus, became compensated externally after 7 more days.

EXAMPLE 27

Chronic Exhaustion Syndrome (CFS)

A 61 year old male patient suffers from chronic exhaustion syndrome. A Paravac injection regimen was stared, administering 0.5 ml Paravac emulsion once every week for 3 months, and then every two weeks for 4 months, and every 2–3 weeks thereafter. Initial beneficial effects could be observed after 8 weeks, and since then the patient feels completely healthy. Treatment was continued to avoid any recidivism, over a period of 9 months.

EXAMPLE 28

Metastatic Rectal Carcinoma 57 year old male patient suffers from metastatic colorectal (rectal) tumor. Injections with a Paravac emulsion were started for a 10 month period, administering 0.5 ml of the Paravac emulsion weekly, and thereafter 3 injections of 0.5 ml each day, every 3 days. Since the increased administration of the dosage the patient feels substantially improved, no further weight loss took place, and the metastasis receded. Treatment was continued for the last 12 months, and is continuing at this time.

We claim:

1. A process for treating systemic inflammatory response syndrome (SIRS), viral diseases, Colitis ulcerosa, Crohn's disease, Parkinson's disease, Alzheimer's disease, multiple sclerosis, infectious hospital polyresistance conditions of viral and bacterial sources (infections hospitalismus), bronchial asthma, kidney and urethral infections, migraines, rheumatoid arthritis, osteoporosis Sudeck, acute and chronic inflammations, venal and arterial inflammations, acute and chronic exhaustion conditions, tumors, muscle shrinkage diseases, hemorrhoids, chemically induced heart diseases, hypertonia, aging phenomena, acute and chronic pain conditions, spastics, polyneuropathies, prostate neoplasms, hair loss, impotence, neurodermitis, cervical syndrome, tissue traumas, and amyotropic lateral sclerosis, which comprises administering to a patient in need therefor an effective amount of Paravac composition.

2. The process of claim 1, wherein said viral infection is hepatitis C, or an acquired immune deficiency disease.

3. The process of claim 1, wherein said Paravac composition comprises in g/ml 0.015 dimethicone 200, 0.015 dimethylsulfoxide, 0.015 sorbitantrioleate, 0.015 cetylstearylalcohol, 0.02 Polysorbate 80, 0.0002 Na/CA salt of ethylenediaminetetraacetic acid, and 0.9 isotonic NaCl solution, and optionally 0.02 glycerol.

4. The process of claim 1, wherein said Paravac composition further comprises at least one of the following intramuscularly or subcutaneously administrable pharmaceutically active agents, antibiotics, corticosteroids, antiparkinson drugs, drugs for treating multiple sclerosis, neuro- or psychopharmaceutically active agents, immunostimulants, and pain killers.

5. The process of claim 1, wherein said administering comprises parenterally injecting a daily plurality of Paravac doses during an initial phase of the process.

6. A Paravac composition which is an oil-in-water emulsion in g/ml of from about 0.01 to about 0.03 polydimethylsiloxane with a polymerization degree of from about 20 to about 400 and a kinematic viscosity of from about 20 to about 1300 $mm^{2/s}$; from about 0.01 to about 0.03 dimethylsulfoxide; from about 0.03 to about 0.06 of a hydrophilic emulsifier; and from about 0.86 to about 0.95 isotonic salt solution, and optionally from about 0.0001 to about 0.01 Na or Ca salt of EDTA as a chelating agent.

7. A Paravac composition as an incomplete adjuvant, which comprises in g/ml 0.015 dimethicone 200, 0.015 dimethylsulfoxide, 0.015 sorbitantrioleate, 0.015 cetylstearylalcohol, 0.02 Polysorbate 80, 0.0002 Na/CA salt of ethylenediaminetetraacetic acid, and 0.9 isotonic NaCl solution, and optionally 0.02 glycerol.

8. The Paravac composition of claim 6, further comprising at least one of the following intramuscularly or subcutaneously administrable pharmaceutically active agents, antibiotics, corticosteroids, antiparkinson drugs, drugs for treating multiple sclerosis, neuro- or psychopharmaceutically active agents, immunostimulants, and pain killers.

9. The Paravac composition of claim 6, as a complete adjuvant further comprising a peptidoglycan strain.

10. The Paravac composition of claim 8, as a complete adjuvant further comprising a peptidoglycan strain.

* * * * *